United States Patent [19]

Tucker

[11] Patent Number: 5,062,425
[45] Date of Patent: Nov. 5, 1991

[54] EXPANSIBLE INTERNAL PRESSURE COLD PACKS AND PERINEAL ICE PAD

[76] Inventor: Annabelle D. Tucker, 4480 Sherman Oaks Cir., Sherman Oaks, Calif. 91403

[21] Appl. No.: 582,663

[22] Filed: Sep. 12, 1990

Related U.S. Application Data

[63] Continuation-in-part of Ser. No. 67,084, Jun. 26, 1987, abandoned.

[51] Int. Cl.⁵ .............................. A61F 7/12
[52] U.S. Cl. ...................... 128/401; 128/400
[58] Field of Search ................. 128/400–403, 128/379; 606/192

[56] References Cited

U.S. PATENT DOCUMENTS

| | | | |
|---|---|---|---|
| 612,724 | 10/1898 | Hamilton | 128/401 |
| 734,213 | 4/1902 | Barnes | 128/401 |
| 4,141,364 | 2/1979 | Schultze | 606/192 |
| 4,240,436 | 12/1980 | Singleton | 128/401 |
| 4,331,151 | 5/1982 | Golden | 128/401 |
| 4,397,315 | 8/1983 | Patel | 128/403 |
| 4,696,302 | 9/1987 | Clark et al. | 128/401 |

FOREIGN PATENT DOCUMENTS

| | | | |
|---|---|---|---|
| 221997 | 8/1966 | Australia . | |
| 1378835 | 3/1988 | U.S.S.R. | 128/401 |
| 1019028 | 2/1966 | United Kingdom . | |

*Primary Examiner*—Edward M. Coven
*Assistant Examiner*—Mark S. Graham

[57] ABSTRACT

An alternative to internal stitches in the care of small bleeders in the vaginally delivered patient that can avoid the chance of a needle stick is the application of direct pressure and cold. An expansible internal pressure cold pack that conforms softly to the contours of a body orifice is inserted prior to inflation. Cold fluid is inserted through a needle insert plug to inflate the bag as the pressure is metered within the vault to apply just enough pressure to avoid or control any small problem after stabilization of any delivery related problem. The inner suspended ice capsule is insulated centrally as the balloon-like bag is inflated to seek out small sulcus or cervical bleeders, hematomas and to deter edema of the traumatized tissue. Attachment of the inner wall of the pack, to suspend the ice capsule centrally, forms vertical drainage channels for body fluid along the bag outer wall. External cold pressure is provided by the perineal pad ice pack to enhance the effectiveness in the deterrent of edema.

10 Claims, 2 Drawing Sheets

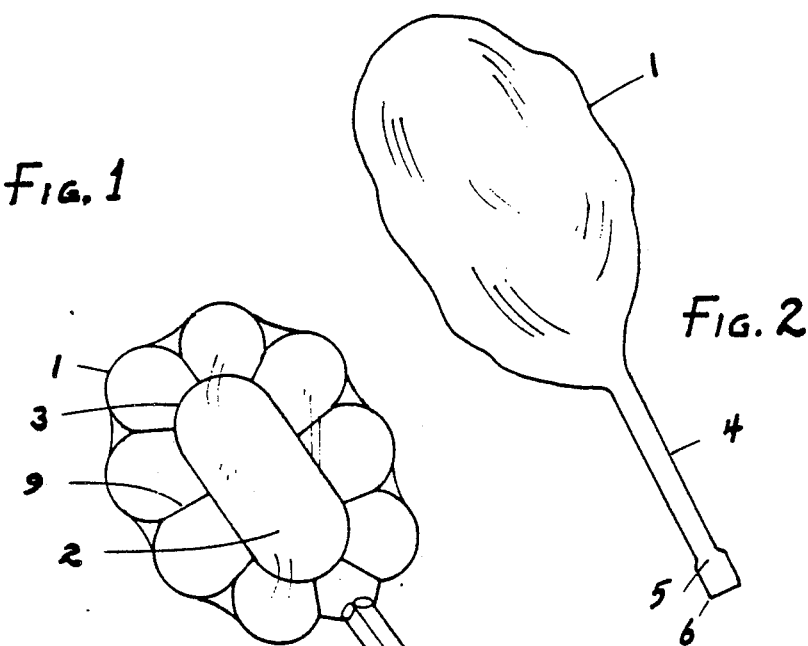
Fig. 1
Fig. 2
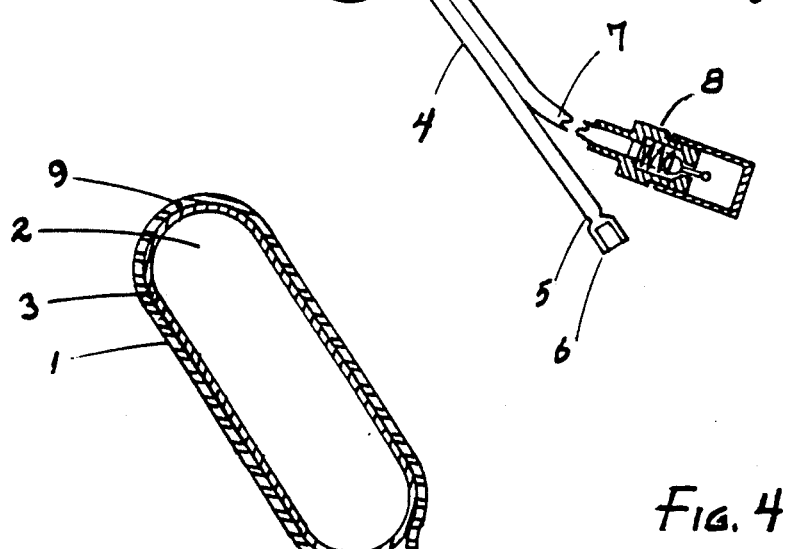
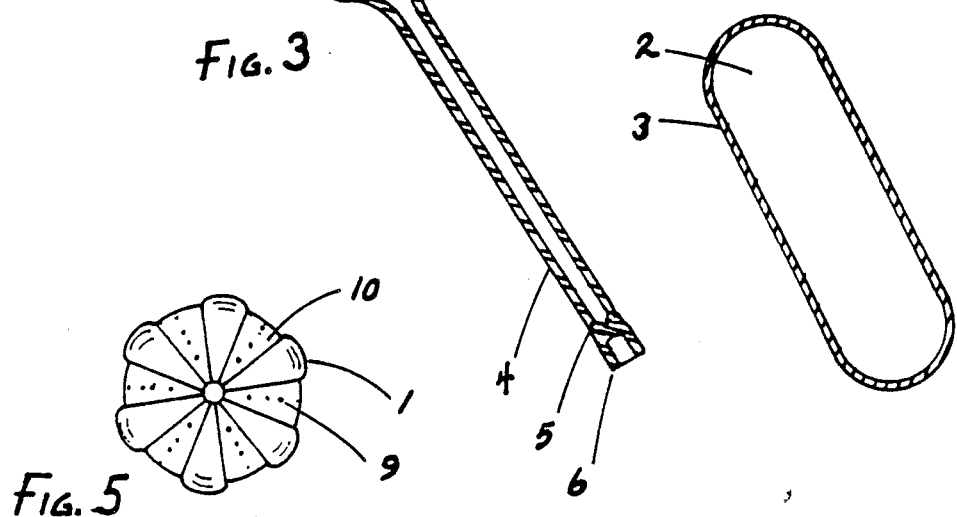
Fig. 3
Fig. 4
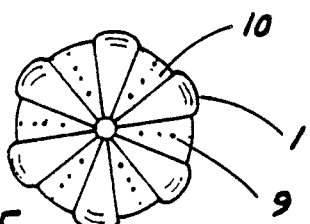
Fig. 5

EXPANSIBLE INTERNAL PRESSURE COLD PACKS AND PERINEAL ICE PAD

RELATED APPLICATIONS

This application is a continuation in-part of application No. 07/067,084 filed 06/26/87, now abandoned.

The parent application—#009,869 filed 2-2-87 Aband. #067,084 filed 6-26-87 Aband. Pet.Rev.

Disclosure Document—#175,497 filed 8-13-87 #181768 filed 11-27-87

BACKGROUND OF THE INVENTION

The present invention relates to an expansible pressure cold pack for the emergency treatment of traumatized tissue within and adjacent to a body orifice to control edema, bleeding and hematomas in the post partum or post operative female patient.

It is desirable to prevent edema immediately post trauma to avoid strain on the tissue and stitches that may perpetuate bleeding or delay healing. It is a further desire to attempt to stop a small bleeder or the increasing size of an existing hematoma with pressure and cold to possibly avoid surgical invasion of already traumatized tissue which also could subject medical personnel to inadvertent needle puncture wounds and subsequent infectious exposure during stitching procedures.

The available inflatable cold packs are of a pre-determined size and shape to contain circulating cold fluid. They are not softly expansible to flexibly fit into the various contours and sizes of a body orifice to equalize pressure on tissues and seek out a sulcus bleeder or hematoma to control it with direct pressure and cold. Present treatment is concerned with freezing the source of bleeding rather than flexible pressure and cold to deter edema as well as the bleeder.

The invention, herein, suggests an expansible pressure cold pack for the various contours and sizes of a body orifice and an exteriorly protected pressure cold pack to provide prevention and control in the treatment of traumatized tissue, therein.

SUMMARY OF THE INVENTION

The primary goals of this invention are to provide an inexpensive, disposable, adjustable size, internal pressure cold pack with a softly expansible rubber body to flexibly apply pressure and cold into the various contours and sizes of a body orifice and an external cold, absorbent pack to prevent and control edema, small bleeders and hematomas of traumatized tissue therein.

In the preferred embodiment of the present invention, a sealed plastic or latex, elongated ice capsule is suspended by attachment along vertical strips within and to the inner body of a softly expandable balloon-like covering. Tissue pressure is provided by the unattached strips of balloon-like bag material that expands in vertical upraised strips leaving channels adjacent to the inner ice capsule that can allow for drainage of body fluids. The bag is expanded by insertion of cold fluid or air through a needle insert plug that seals the distal end of a small tubular extension continuous with the interior of the balloon body that provides a thicker bodied filling tube.

A further goal of this invention is to provide a pressure cold pack whose sealed, inner suspended, ice capsule can be kept frozen by storing the device in its sterile packaging near the emergency center where it is readily and portably available for immediate use as a preventive procedure for traumatized tissue.

Another goal of this invention is to provide a pressure cold pack that is self contained and elastic enough to give with body movement to allow transport of the patient in comfort and ease, with treatment uninterrupted.

An additional goal of this invention is to provide a sealed pressurized cold pack whose internal pressure is measured by the pressure on internal tissue and stabilizes within the bag to provide continuous, equalized and steady pressure directly against a bleeding area even with patient movement.

A further goal of this invention is to provide an external pressure cold perineal pad to reinforce the internal cold pressure to deter external edema or a perineal bleeder while absorbing body fluid drainage. The wait belt has clamping, means to allow cinching up each end of the perineal ice capsule pad to control pressure against perineum and to maintain that pressure.

Another goal of this invention is to provide heat exchange means within the expansible internal pressure cold pack by suspending centrally a pre-frozen ice capsule that continues to chill the fluid used to inflate the pack after it is inserted into a body cavity to maintain the cold atmosphere within the body cavity and the outer surface of the pack.

A further goal of this invention is to provide an exterior gauge that allows one to monitor pressure build up within the body orifice as the bag is being filled with cold fluid or air. The interior of the gauge is a sealed continuation of the interior of the bag, dividing the extension filling tube into two channels that separate channel walls at the distal end to provide access to the needle insert plug and a clear view of the pressure gauge as two distinct tubular ends.

Another goal of this invention is to provide an expansible pressure cold pack whose vertical drainage channels are formed by spot attachment of the outer bag wall to the inner sealed ice capsule wall to allow fluid to cross over channel spot attachment and equalize internal fluid pressure as the pack is filled with cold fluid.

Further features and advantages of this invention will become more apparent from the following description, the appended claims, and the drawings.

BRIEF DESCRIPTION OF THE DRAWINGS

The accompanying drawings illustrate the invention. In such drawings:

FIG. 1 is a top plan cross sectional view of the expansible bag and the suspended inner ice capsule of the present invention.

FIG. 2 is a top plan view of the expansible bag.

FIG. 3 is a cross sectional view of the uninflated bag of FIG. 2 showing the inner suspended and attached ice capsule.

FIG. 4 shows a cross sectional view of ice capsule separate from the expansible bag.

FIG. 5 is a side elevational view of the expansible bag showing channels formed by attachment to inner ice capsule.

DETAILED DESCRIPTION OF THE PREFERRED EMBODIMENTS

Figure 6:
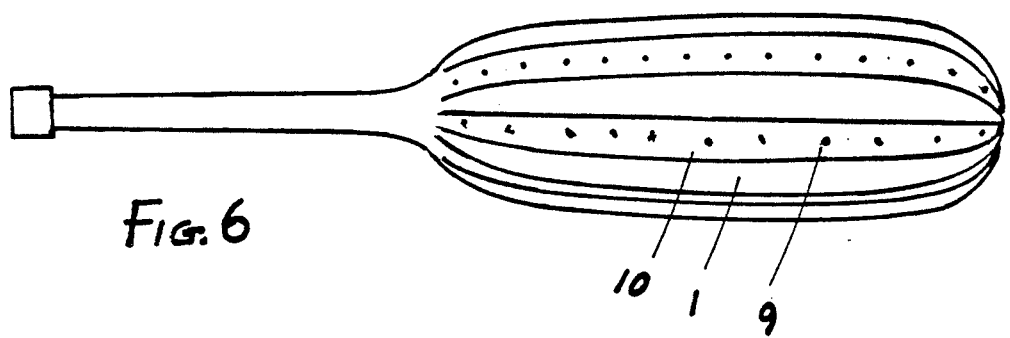
FIG. 6 is a perspective view of the expansible pressure cold pack showing the vertical drainage channels and the filling tube with its needle insert plug.

Referring now to FIG. 1 there is shown a cross sectional view of the expansible pressure cold pack having an outer cover 1, an internal sealed fluid filled capsule 2 with its suspension means 9 that attaches the outer surface of wall 3 to the inner surface of the expansible outer cover 1, a divided filling tube 4 and 7 whose separated sealed distal ends embody a needle insert plug 5 within one end and a spring loaded pressure gauge 8 within a separate distal end with said filling tube 4 and 7 being made to form a thicker walled extention of the outer cover and internally in fluid communication with that outer cover 1.

In FIG. 2 there is shown a flat view of an expanded pressure cold pack with an extended filling tube 4, a needle insert plug 5 at the distal end and a gripping cuff 6 that is an extension of the filling tube material that is turned up on itself. A version of the bag which omits the inner fluid capsule may be considered a simplification and economical means of the concept that can be deflated for body drainage of captured fluid and refilled with cold fluid to provide the cold pressure to the traumatized internal orifice.

The conical shape of the uninflated expansible internal pressure cold pack with the inner suspended ice capsule 2 is shown in FIG. 3. The suspension means 9 is in close proximity to the inner wall of the cover 1 and the inner wall 3 which surrounds the ice capsule. It aligns vertically with space between each suspension means 9 to allow fluid to expand the outer bag chambers defined by the vertical attachments of the suspension means9 with equal pressure. Drainage channels 10 (see FIG. 6) are formed on the outer surface of the expansible pressure cold pack by the vertical attachment of the outer bag 1 to the inner ice capsule 2 using suspension means 9, which are preferably made of elastic rubber threads but may be attached by spot welding the inner wall of the bag to the capsule wall directly. When the outer cover 1 is inflated with cold fluid or air by a needle inserted into the provided plug 5 at the end of the filling tube 4, these drainage channels 10 will become defined during inflation.

Figure 8:
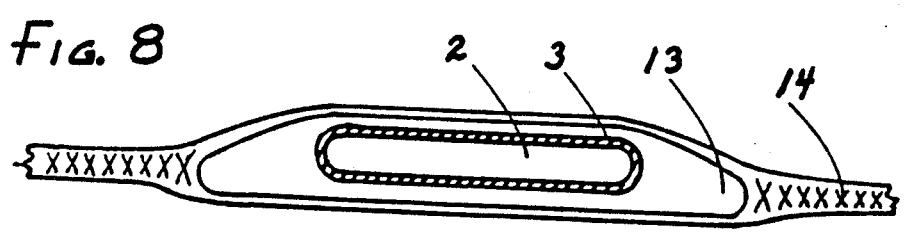
FIG. 8 shows a cross sectional view of the sealed ice capsule as a part of a perineal pad cover providing an external pressure cold pack.

The inner ice capsule 2 is shown in FIG. 4 with the outer wall 3 as a double wall or a thicker plastic or latex material to provide insulation if used in approximation with skin surface. The sealed fluid capsule 2 is kept frozen for emergency availability and can be used separate from the described attachment that uses suspension means 9 within the body of the expansible internal pressure cold pack's outer cover 1. It can be made a part of the pressure cold pad as shown in FIG. 8. The ice capsule 2 may be end sealed to provide a smooth walled bag to avoid tissue irritation if used in approximation with the skin surface. The end seal may be a fluid insert valve or plug to allow closer control of the internal fluid pressure within the ice capsule prior to being frozen.

A side elevation view of the expansible pressure cold pack depicted in FIG. 3 and FIG. 6 is shown in FIG. 5. The drainage channels 10 for body fluid are shown to be formed by the close proximity of the vertical suspension means 9. The expansible body 1 conforms to the attachments and takes the shape of vertical strips that provide internal chambers that can be expanded when fluid filled. The suspension means 9 support the inner ice capsule in central suspension. The internal chambers define flowpath volumes through which injected cold fluid travels and accumulates.

FIG. 6 shows a side perspective view of the expansible internal pressure cold pack with its drainage channels 10 in substantially parallel alignment along the outer walls of the outer cover 1. The channels 10 are formed in this instance by spot welds along the channel 10 to attach the outer cover 1 to the inner wall 3 with heat means rather than suspension threads 9 The filling tube 4 is shown as a single tube that embodies the needle insert plug or fluid insert valve 5 within its distal end and in fluid communication with the interior of the outer bag 1.

Figure 7:
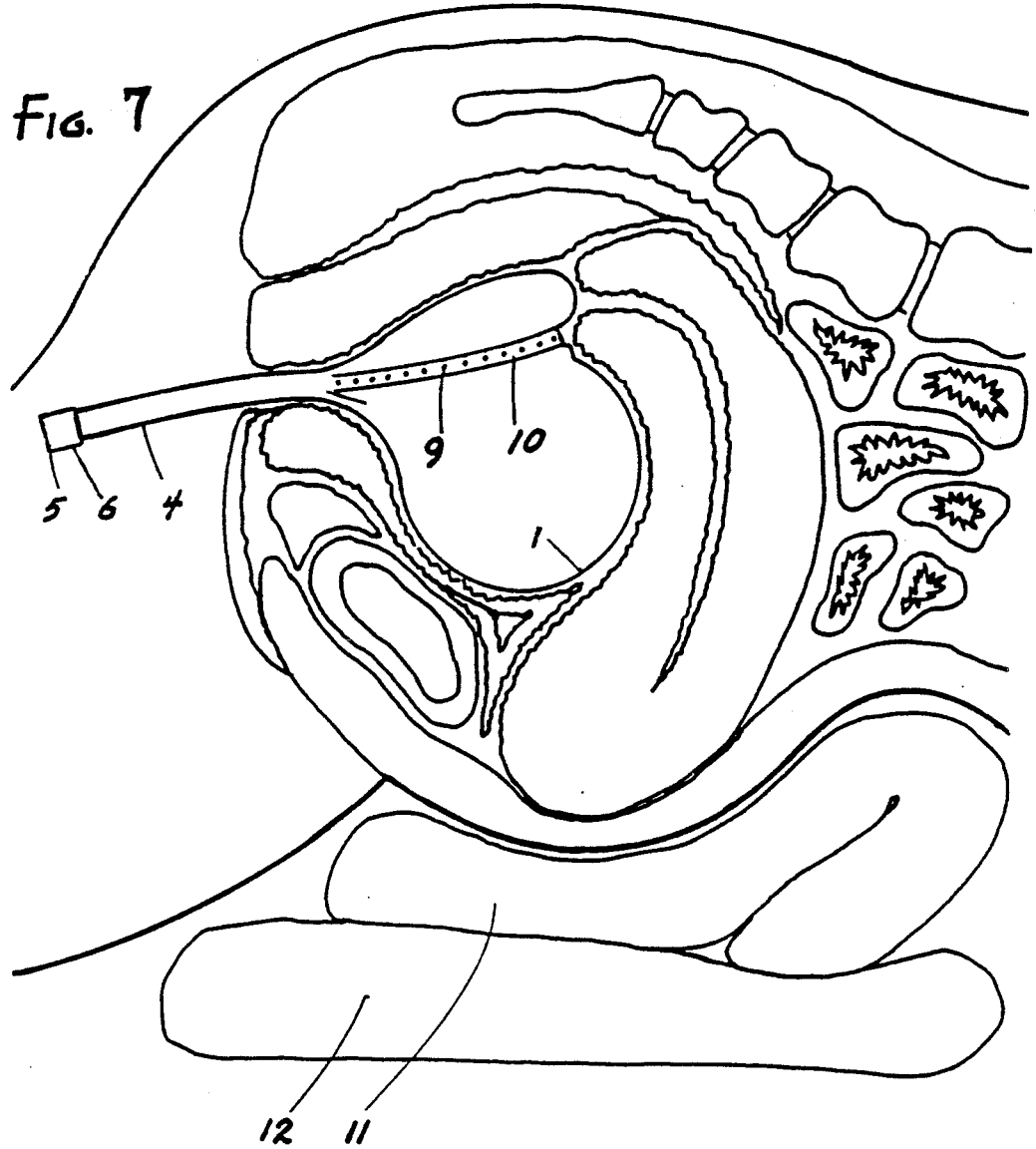
FIG. 7 shows the expansible pressure cold pack inflated within the vaginal vault with the patient in prone position over the support pillows placed in fundal position.

In FIG. 7 there is shown the inflated expansible internal pressure cold pack 1 inserted into place within the vaginal vault with the drainage channels positioned in approximation to the cervical outlet of the uterus to capture and direct outward flow of drainage. The flexible walls of the rubber balloon-like bag closely conforms to the contours of the internal orifice to reach sulcus bleeders or hematomas and equalize tissue pressure to deter their progress and stop edema. The filling tube 4 remains externally accessible. Folded pillows 11 and 12 are shown in fundal position to maintain a firm fundus and prevent uterine bleeding and to enhance the internal pressure from the pressure cold pack 1 in the post partum patient.

When it is desirable to utilize the internal ice capsule 2 apart from the outer cover 1, the ice capsule 2, shown in FIG. 8 is placed within an absorbant perineal pad 13 with a layer of the absorbant material acting as insulation against skin contact with the iced surface that can cause burns on the traumatized tissue. Cold pressure can be thus provided when the waist belt attached and adjustably clamped at each end of the perineal ice pad is cinched up to increase the pressure against the perineal and rectal tissue to deter edema and thus avoid pain. The surrounding pad material 13 absorbs the drainage and holds the ice capsule 2 in place against the traumatized tissue of the post partum patient or other perineal traumatized patient.

Thus, while the present invention has been described, with respect to an exemplary embodiment thereof, it will be understood by those of ordinary skill in the art that variations and modifications can be effected within the scope and spirit of the invention.

I CLAIM:

1. An inflatable, expandable device to fit into various contours and sizes of a body cavity for the purpose of providing pressure and cold against traumatized tissue in the prevention of edema, bleeding and hematomas, comprising:

an outer cover comprising an elastic material, said elastic material being expandable and stretchable such that, upon inflation of said outer cover, the elastic material will substantially conform to interior shapes of the body cavity thereabout, said outer cover defining an interior volume therein;

an ice capsule pack comprising inner walls which are enclosed within the interior volume defined by the outer cover, said interior walls also defining a sealed enclosed volume, said enclosed volume having frozen fluid therein such that said inner walls encapsulate the frozen fluid, wherein said frozen fluid is frozen into solid form prior to insertion of said device into the body cavity, wherein said inner walls and said outer cover define a flow path volume therebetween and wherein said device further includes suspension means for attaching said outer cover to a plurality of locations on said inner walls; access means for allowing a fluid substance to be introduced into said flowpath volume; and a cold fluid substance within said flowpath volume, said fluid substance being present in a quantity suitable for maintaining the outer cover in an inflated, expanded state having a configuration matching the interior contours of the body cavity.

2. A device as set forth in claim 1, wherein said access means comprises a tubular extension that is integrally formed with said outer cover and that is in fluid communication with the flowpath volume defined within said outer cover, said tubular extension having a needle tip insert plug at a distal end thereof, said needle tip insert plug providing diaphragm means for closure of said distal end when said insert plug is not accomodating a needle tip.

3. A device as set forth in claim 2, wherein said tubular extension has an elongated length such that said tubular extension will protrude from a human body while said device is being accommodated within the body cavity.

4. A device as set forth in claim 2, wherein said tubular extension defines an internal volume that is divided by barrier means for separating said tubular extension into a first channel and a second channel, wherein both the first and second channels are in fluid communication with the interior of the outer cover, and wherein said first channel terminates in the distal end having a needle tip insert plug, and wherein said second channel terminates in a distal end having pressure gauge means associated therewith, said device further including this pressure gauge means for measuring internal pressure within the outer cover, said internal pressure being provided by said cold fluid substance.

5. A device as set forth in claim 1, further including means for allowing fluid drainage along exterior surfaces of the outer cover.

6. A device as set forth in claim 2, wherein said suspension means comprises a plurality of elastic threads.

7. A device as set forth in claim 6, wherein said elastic threads attach said outer cover and said inner walls at a plurality of locations such that said outer cover is configured into a shape that defines a plurality of drainage channels along exterior surfaces thereof.

8. A device as set forth in claim 1, wherein said inner walls are comprised of an elastic material.

9. A device as set forth in claim 1, wherein said suspension means suspend said ice capsule pack within said outer cover.

10. A device as set forth in claim 2, wherein said tubular extension is comprised of a tubular wall of thicker outer cover material and having a portion which is doubled back upon itself at said distal end of the tubular extension, said doubled tubular wall portion defining a cuff for manually gripping the needle tip insert plug.

* * * * *